United States Patent [19]
Daniels et al.

[11] Patent Number: 5,653,758
[45] Date of Patent: Aug. 5, 1997

[54] METHOD OF USING A RADIOLUCENT ORGAN DISPLACEMENT DEVICE FOR RADIATION THERAPY

[75] Inventors: John R. Daniels, Pacific Palisades, Calif.; Terry R. Knapp, Neuchatel, Switzerland

[73] Assignee: LipoMatrix, Incorporated, Tortola, Virgin Islands (Br.)

[21] Appl. No.: 469,479

[22] Filed: Jun. 6, 1995

Related U.S. Application Data

[63] Continuation of Ser. No. 284,899, Aug. 2, 1994, abandoned, which is a continuation of Ser. No. 977,891, Nov. 18, 1992, abandoned.

[51] Int. Cl.$^6$ .................. A61F 2/02; A61F 2/12; A61F 2/54; A61B 19/00
[52] U.S. Cl. .................. 623/11; 623/8; 623/66; 128/898
[58] Field of Search .................. 623/7, 8, 11, 66; 128/653.1, 659, 898; 378/62–69, 156, 204

[56] References Cited

U.S. PATENT DOCUMENTS

| | | |
|---|---|---|
| 3,293,663 | 12/1966 | Cronin . |
| 3,665,520 | 5/1972 | Perras et al. . |
| 3,954,102 | 5/1976 | Buuck . |
| 4,197,846 | 4/1980 | Bucalo . |
| 4,205,401 | 6/1980 | Frisch . |
| 4,298,998 | 11/1981 | Naficy . |
| 4,550,720 | 11/1985 | Trick . |
| 4,592,755 | 6/1986 | Penton et al. . |
| 4,605,691 | 8/1986 | Balazs et al. . |
| 4,636,213 | 1/1987 | Pakiam . |
| 4,648,880 | 3/1987 | Brauman . |
| 4,671,255 | 6/1987 | Dubrul et al. . |
| 4,694,827 | 9/1987 | Weiner et al. .................. 128/303 R |
| 4,731,081 | 3/1988 | Tiffany et al. . |
| 4,795,463 | 1/1989 | Gerow .................. 623/8 |
| 4,863,470 | 9/1989 | Carter . |
| 4,899,764 | 2/1990 | Gauger et al. . |
| 4,904,260 | 2/1990 | Ray et al. . |
| 4,995,882 | 2/1991 | Destouet et al. . |
| 5,067,965 | 11/1991 | Ersek et al. . |
| 5,101,813 | 4/1992 | Trick . |
| 5,133,742 | 7/1992 | Pinchuk . |
| 5,258,026 | 11/1993 | Johnson et al. .................. 623/8 |
| 5,391,203 | 2/1995 | Bartlett et al. . |
| 5,396,117 | 3/1995 | Pinchuk et al. . |

FOREIGN PATENT DOCUMENTS

| | | |
|---|---|---|
| 0 177 288 | 4/1986 | European Pat. Off. . |
| 2192546 | 1/1988 | United Kingdom . |

*Primary Examiner*—Debra S. Brittingham
*Attorney, Agent, or Firm*—Howell & Haferkamp, L.C.

[57] ABSTRACT

A temporarily implantable organ displacement implant is comprised of a bladder with a one-way valve for being filled with a fluid for displacement of a healthy organ from a tissue site desired to be irradiated by radiation therapy. This organ displacement implant is substantially radiolucent which thereby facilitates its placement and minimizes its interference with the radiation therapy.

5 Claims, 1 Drawing Sheet

METHOD OF USING A RADIOLUCENT ORGAN DISPLACEMENT DEVICE FOR RADIATION THERAPY

CROSS-REFERENCE TO RELATED APPLICATION

This application is a continuation of application Ser. No. 08/284,899, filed on Aug. 2, 1994, now abandoned, which is a continuation of application Ser. No. 07/977,891, filed on Nov. 18, 1992, now abandoned.

BACKGROUND AND SUMMARY OF THE INVENTION

Radiation therapy is presently one of the major options for treatment of cancer. As well known in the art, radiation therapy involves radiating cancer growths and tissue sites in order to kill the cancer and prevent its spread throughout the body. This therapy is typically used for many different kinds of cancer, including those cancers attacking the internal organs of a human such as the prostate gland, uterus, and pelvic lymph nodes. Because of the obvious harmful effects of radiation which is inadvertently exposed to healthy tissue, there has been much effort in the prior art directed to preventing this from occurring. Principally, this effort has been directed to more exactly locating the tissue site intended to receive the therapy, and more precisely irradiating that site with a controlled energy beam. Efforts in these areas continue. However, because of the dynamic nature of the human body, and the present limitations of radiation techniques, there still remains a significant risk of injury or morbidity for body organs or tissues surrounding the cancerous site.

In an effort to advance the art in this area, and to aid in minimizing, and in some instances even eliminating, inadvertent and unintended radiation of healthy organs and tissues, the inventors herein have succeeded in designing and developing a surgical implant for temporary implantation for separating or isolating healthy tissues and organs from cancerous tissues and organs. This implant is radiolucent, even at radiation levels significantly below that ordinarily used for many kinds of radiation treatment, and is essentially comprised of an inflatable bladder having a valve which permits the bladder to be filled in situ with a radiolucent filler material. With the implant of the present invention, not only is there achieved a clear separation between the healthy and unhealthy tissue sites, but the implant is virtually invisible to the therapy so that virtually no adjustment in the therapy is required when the implant is used. As is well known in the art, radiation therapy protocol involve a series of treatments each of which comprises the timed irradiation of a tissue site with a very carefully calculated radiation dosage. These calculations can be quite sensitive in order to reliably kill the cancerous growth while at the same time minimizing injury and morbidity to surrounding healthy tissue. The use of the implant of the present invention will have minimal effect on these calculated radiation therapy protocols.

The implant's position may also be readily monitored by x-ray and will also permit the continued use of x-ray to view those tissue sites desired to be viewed as the implant is virtually transparent at these reduced energy levels used for x-ray as well. Therefore, the implant may be readily and effectively used without interfering with either the therapy itself, or a monitoring of the tissue sites to determine the effects of therapy as therapy progresses.

The implant is itself comprised of a generally elastomeric bladder with a one-way fill valve. The bladder may be made of a silicone/polyurethane composite and the filler material may be a highly purified and sterile neutral triglyceride derived from soybean oil. Alternative materials may also be used, as explained below. The bladder may be readily filled via a silicone rubber fill tube which mates with the diaphragm one-way fill valve in the bladder/shell. The proximal end of the fill tube may mate with a triglyceride containing fill cartridge, or a fill gun or syringe may be used to deliver the filler material into the bladder/shell. The size and/or shape of the bladder may be readily sized and fitted to the particular tissue site and application. No particular size and/or shape is required in order to achieve the benefits of the present invention.

As noted above, the implant may be surgically implanted at the time of initial exploration or later as part of the therapy itself. Also, the implant may be implanted in an inflated and filled condition or may be implanted and filled in situ. Explantation may be via endoscopic means on an out-patient basis.

While the principal advantages and features of the invention have been explained above, a more thorough understanding may be attained by referring to the drawings and description of the preferred embodiment which follow.

DETAILED DESCRIPTION OF THE PREFERRED EMBODIMENT

Figure 1:
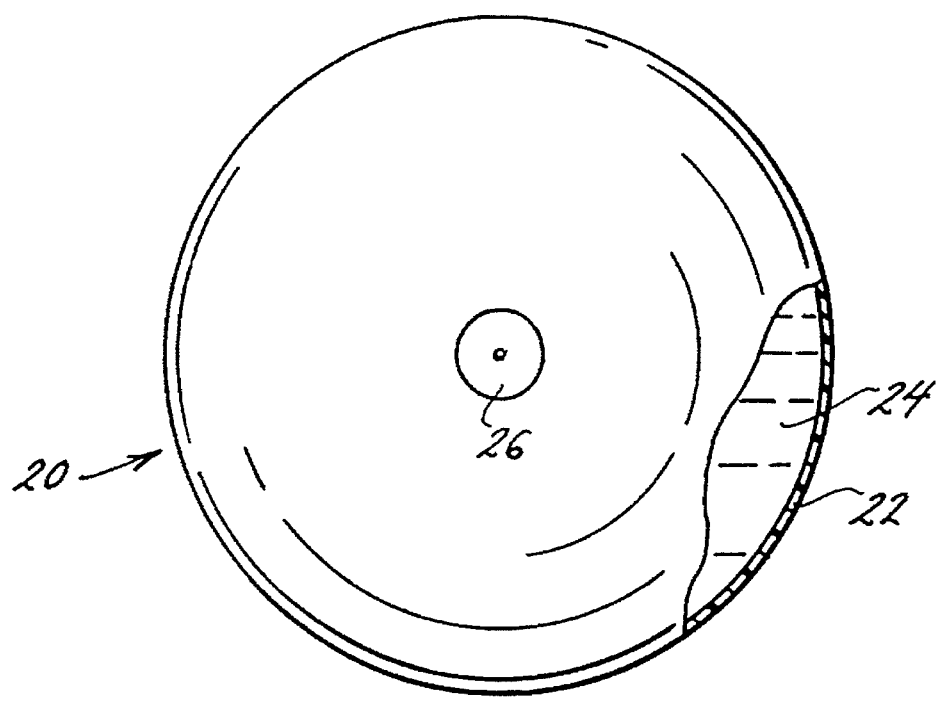
FIG. 1 depicts a generally spherical implant of the present invention.
Figure 2:
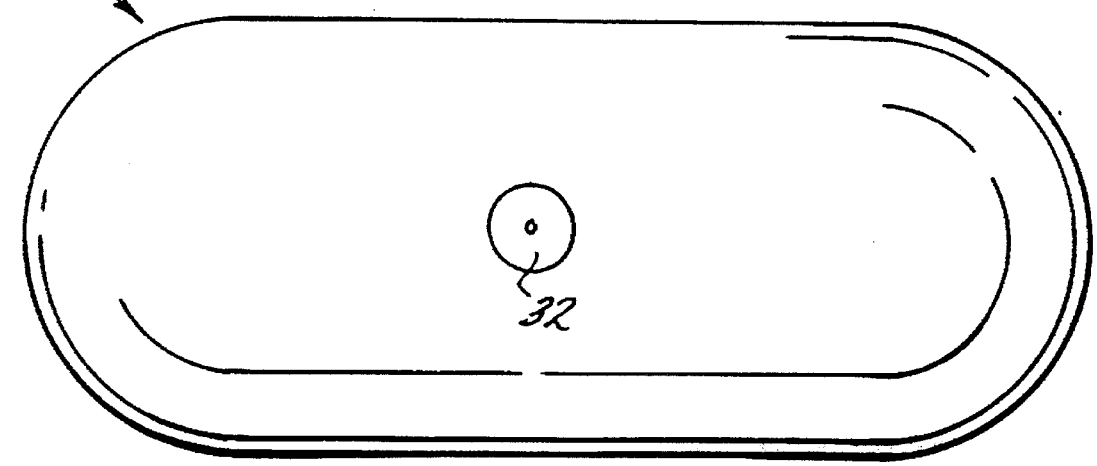
FIG. 2 depicts a generally elliptical implant of the present invention.

The temporary surgical implant 20 of the present invention is shown in FIG. 1 and is generally spherically shaped, although its spherical shape is a matter of design and is only chosen as being exemplary hereof. The implant 20 is comprised of a bladder-like shell 22 which is filled with a filler material 24 through a one-way valve 26. The bladder-like shell may be made of a silicone/polyurethane composite elastomer and the filler material 24 may be purified and sterile neutral triglyceride derived from soybean oil. Alternately, the bladder 22 may be made from any one or more of the following materials: linear aliphatic polyether urethane; linear aliphatic polyester urethane; cyclic aliphatic polyether urethane; cyclic aliphatic polyester urethane; aromatic polyether urethane; aromatic polyester urethane; polybutylene; polypropylene; crosslinked olefinic elastomers; and styrene-ethylene/butylene-styrene block copolymer. Also, the filler material 24 may be principally comprised of any one or more of the following materials: peanut oil, sunflower seed oil, .or any other suitable fluid with the same atomic number as fatty tissue, $Z=6.0$.

The implant 20 is substantially radiolucent at reduced levels of radiation energy. This radiolucency is readily achieved by any material which has an effective atomic number (Z) which is substantially equal to 6.0 within a range of $\pm 0.5$. It is well known and understood in the art that virtually any material is radiolucent presuming that the energy level of the x-ray (for example) is increased to an appropriate level. However, radiolucency at reduced levels, such as is used for mammography, is not as readily achieved and such reduced level radiolucency is intended for optimum effect with the present invention. Another benefit of using the filler materials disclosed herein is that they are all considered to be biocompatible.

The construction and composition of the present invention facilitates endoscopic implantation and explantation. This minimally invasive technique is thus thought to be capable of being performed on an out-patient basis. This will therefore enhance the usefulness of the present invention by reducing its cost and inconvenience.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A method for isolating a tissue site within a patient's body for therapeutic radiation therapy, the method comprising the steps of:

identifying the tissue site to be isolated;

spacing said tissue site from other body tissue by inserting an implant to thereby isolate said tissue site and reduce a likelihood of unintended exposure of said other body tissue to said therapeutic radiation therapy; and irradiating said tissue site as prescribed by said therapeutic radiation therapy.

2. The method of claim 1 further comprising the step of inflating the implant with a filler material to thereby expand said implant.

3. The method of claim 2 wherein the step of inflating the implant follows the step of inserting the implant.

4. The method of claim 2 further comprising the step of removing the implant after radiating said tissue site.

5. The method of claim 4 wherein the step of removing the implant includes removing the implant by endoscopic means.

* * * * *